(12) United States Patent
Leonhardt et al.

(10) Patent No.: US 7,483,749 B2
(45) Date of Patent: Jan. 27, 2009

(54) METHOD OF ENHANCING MYOGENESIS BY ELECTRICAL STIMULATION

(75) Inventors: Howard J. Leonhardt, Weston, FL (US); Juan C. Chachques, Paris (FR)

(73) Assignee: Bioheart, Inc., Sunrise, FL (US)

( * ) Notice: Subject to any disclaimer, the term of this patent is extended or adjusted under 35 U.S.C. 154(b) by 308 days.

(21) Appl. No.: 11/091,554

(22) Filed: Mar. 28, 2005

(65) Prior Publication Data

US 2005/0171578 A1    Aug. 4, 2005

Related U.S. Application Data

(63) Continuation of application No. 10/171,051, filed on Jun. 13, 2002, now abandoned.

(60) Provisional application No. 60/297,913, filed on Jun. 13, 2001.

(51) Int. Cl.
*A61N 1/08* (2006.01)

(52) U.S. Cl. ....................................................... 607/50

(58) Field of Classification Search ...................... 607/50
See application file for complete search history.

(56) References Cited

U.S. PATENT DOCUMENTS

| | | | |
|---|---|---|---|
| 5,130,141 A | | 7/1992 | Law et al. |
| 5,602,301 A | | 2/1997 | Field |
| 6,151,525 A | * | 11/2000 | Soykan et al. .................. 607/50 |
| 2002/0124855 A1 | * | 9/2002 | Chachques .................. 128/898 |
| 2003/0103951 A1 | * | 6/2003 | Pittenger et al. .......... 424/93.21 |
| 2003/0125615 A1 | * | 7/2003 | Schwartz ..................... 600/374 |

* cited by examiner

*Primary Examiner*—George R Evanisko
*Assistant Examiner*—Joseph Stoklosa
(74) *Attorney, Agent, or Firm*—Hodgson Russ LLP

(57) ABSTRACT

The present invention provides a method for enhancing regeneration of the myocardium. The method comprises the steps of applying electrical stimulation to an injury site in the myocardium. The method can be used in combination with implantation of myogenic cells into the injury site. The electrical stimulation may be applied before or after the implantation.

8 Claims, No Drawings

METHOD OF ENHANCING MYOGENESIS BY ELECTRICAL STIMULATION

This application is a continuation of U.S. patent application Ser. No. 10/171,051, filed on Jun. 13, 2002, now abandoned, which claims priority to U.S. provisional application Ser. No. 60/297,913 filed on Jun. 13, 2001, the disclosures of which are incorporated herein by reference.

FIELD OF THE INVENTION

This invention relates generally to the field of heart muscle degeneration. More particularly, this invention provides a method for enhancing myogenesis by electrical stimulation.

BACKGROUND OF THE INVENTION

There is an important need for novel therapies to treat heart failure. The use of pharmacological therapies has improved survival in heart failure patients. Additionally, new mechanical assist devices and xenotransplantation approaches are currently being developed yet mortality remains high, with more than 50% of all patients succumbing within 5 years of initial diagnosis. The utility of cardiac transplantation is limited by shortage of donor hearts, the complications of immunosuppression, and the failure of grafted organs.

The molecular basis for the syndrome of congestive heart failure is a lack of stem cells in the myocardium and the inability of the damaged heart cells to undergo repair or divide. The idea of transplanting single cells instead of entire organ has a number of attractive attributes and is dependent on an ever expanding understanding of molecular basis of skeletal myogenesis.

Heart failure remains a significant public health problem in contemporary cardiology. Prevalence of heart failure, estimated between 1% and 4% of the population, increases exponentially with age, so that current demographic trends in industrialized nations predict an increase in the number of patients with heart failure during coming decades as the populations of these countries grow older.

Heart failure is associated with significant morbidity, a high incidence of complications, frequent hospitalization, and rising healthcare costs. Mortality and morbidity caused by cardiac insufficiency are increasing at a time when the overall cardiovascular death rate is on the decline. In the United States alone, an estimated 2.5-4 million individuals have a diagnosis of "congestive heart failure", and an additional 400,000-500,000 new cases are diagnosed annually.

A large proportion of the end stage heart failure patients need a therapeutic approach other than the current standard modalities, due to the restricted number of heart donors for heart transplantation and the high cost and drawbacks of mechanical assist devices. Approximately, 25% of patients included in waiting lists for heart transplantation die, due to the limited donor availability.

Congestive cardiac failure is caused by a decrease in myocardial contractility due to mechanical overload or by an initial defect in the myocardial fiber. The alteration in diastolic function is inextricably linked with the pathophysiology of cardiac insufficiency. Despite a widely varying and diverse etiology of congestive cardiac failure (e.g. ischemic or idiopathic dilated cardiomyopathies), the pathophysiology is to a great extent constant. The predominant factor is the alteration of myocardial contractility. This contractility defect causes an elevation of the ventricular wall tension resulting in a progressive decline in the contractile state of the myocardial fibers.

Heart failure involves in many cases defects of the heart conduction system as well as depressed myocardium contractility together with enlarged ventricular cavities. Heart failure patient death is either due to pump failure or to arrhythmia (sudden death—ventricular tachycardia/ventricular fibrillation.

Cell transplantation strategies have been designed to replace damaged myocardial cells with cells that can perform cardiac work. The cellular cardiomyoplasty procedure consists in transplanting cultured satellite cells (myoblasts), originated from a skeletal muscle biosy of leg or arms of the same individual, to the sick myocardium. Satellite cells are mononucleated cells situated between the sarcolemma and the basal lamina of differentiated muscle fibers. They are thought to be responsible for postnatal growth, muscle fiber repair and regeneration. Another approach for cellular cardiomyoplasty consists in the utilization of bone marrow stem cells, autologous or foetal cardiomyocytes, or smooth muscle cells.

One of the problems limiting hemodynamic benefits of cellular cardiomyoplasty is that even if the myoblasts survived after implantation, functionally this cells cannot contract spontaneously, hence, they do not contribute to improve regional myocardial contractility. Mechanical and electrical coupling of the transplanted myoblasts with the cardiomyocytes is still not clear.

SUMMARY OF THE INVENTION

This invention provides a method for enhancing myogenesis in the injured myocardium. The method comprises the steps of identifying an injury or degeneration site in the myocardium and applying electrical stimulation to the site to enhance myogenesis. This method can be used in combination with implantation of myogenic cells into the myocardium.

DETAILED DESCRIPTION OF THE INVENTION

The term "myogenic cells" as used herein means a cells that normally differentiates into cardiomyoblasts or cardiomyocytes or can be induced to differentiate into cardiomyoblasts or cardiomyocytes or can carry out the functions attributable to cardiomyoblasts or cardiomyocytes.

The present invention provides a method for the enhancement of myogenesis by electrical stimulation. The method comprises providing electrical stimuli to an injury site to stimulate regeneration. The electrical stimulation may be used alone or together with transplantation of cultured myogenic cells into the injured region. The electrical stimulation may be applied before of after the transplantation of myogenic cells.

The electrical stimulation may be applied by standard electrodes, (such as silver electrodes) as a direct current. Suitable voltages for this invention include between 1 to 40 mV. An example of a suitable voltage is 30 mV/few hundred nanometers. In one embodiment, the direction of the current is reversed after a few days. In another embodiment, for recruitment and protein release purposes, a current of 200 to 700 picoamps is provided at 15 pulse beats per second with positive polarity and a voltage of 7 mV. In another embodiment, a current of 700 to 1500 picoamps with drop 200 picoamps after 1 minute for 10 seconds and then back to 700 to 1500 for another minute, with 30 pulse beats per second, negative polarity with a voltage of 3.5 mV is provided. In yet another embodiment, for cell culture applications, a current of 500 picoamps with 70 pulsation beats per minute bath pulsation, positive polarity and 15 mV can be used. Cells are preferably plated on collagen coated substrates and stretched 0.2 mms at 70 beats per minute.

Although not intending to be bound by any particular theory, it is considered that stimulation recruits stem cells from bone marrow to the injury site and aides in their differentiation into muscle cells. The stimuli may also dedifferentiate some of the fibroblasts into more primitive cells so that they are then able to differentiate into muscle cells, particularly when immature myoblasts and cardiomyocytes are injected into the region. The electrical stimuli may also help myoblasts to form electrical connections (gap junctions/intercalated discs) with the host myocardium.

Although not intending to be bound by any particular theory, it is believed that the regrowth phase is divided into two parts; the first phase begins with the cleanup of wound debris by phagocytes and culminates in the dedifferentiation of tissue (fibroblasts) to form a blastema. Redifferentiation and orderly growth of repair cells (stem cells recruited from bone marrow, dedifferentiated fibroblasts, injected myoblasts, injected cardiomyocytes) are stimulated to form muscle from signals of the microenvironment.

In one embodiment of the invention, electrical stimulation is applied to myoblasts and cardiomyocytes in culture to accelerate the rate of expansion of the myoblasts in culture and to stimulate the formation of gap junctions between transplanted myoblasts and the host myocardium.

A supply of myoblasts or cardiomyocytes for transplantation into the injured region of the heart can be prepared by techniques disclosed in U.S. Pat. Nos. 5,130,141; 5,602,301 and 6,151,525, which disclosures are hereby incorporated herein by reference.

What is claimed is:

1. A method of enhancing myogenesis in myocardium comprising the steps of:
    identifying an injury site in the myocardium; and applying electrical stimulation to the site, wherein the application of the electrical stimulation causes myogenesis, wherein the electrical stimulation is provided as 30 pulses per second with a voltage of 3.5 mV, and successively alternating currents of 700 to 1500 picoamps for one minute, 200 picoamps for 10 seconds, and again with 700 to 1500 picoamps for one minute.

2. The method of claim 1, wherein the electrical stimulation recruits stem cells to the injury site.

3. The method of claim 1, wherein the direction of the current of the electrostimulation is periodically reversed.

4. The method of claim 1, further comprising the step of implanting myogenic cells into the site of injury before or after application of electrical stimulation.

5. The method of claim 4, wherein the myogenic cells are first electrostimulated in culture.

6. The method of claim 5, wherein the cells are electrostimulated with 15 mV and a current of 500 picoamps at 70 pulses per minute.

7. The method of claim 5, wherein the cells are plated on collagen coated substrates.

8. The method of claim 5, wherein the cells are stretched 0.2 mms at 70 beats per minute.

* * * * *